US005635208A

United States Patent [19]
Parekh et al.

[11] Patent Number: 5,635,208
[45] Date of Patent: Jun. 3, 1997

[54] GRANULATION PROCESS FOR PRODUCING AN ACETAMINOPHEN AND DIPHENHYDRAMINE HYDROCHLORIDE COMPOSITION AND COMPOSITION PRODUCED BY SAME

[75] Inventors: Kishor B. Parekh, Horsham; Peter F. Eisenhardt, Philadelphia; Robert Hitchner, Perkasie, all of Pa.

[73] Assignee: McNeil-PPC, Inc., Skillman, N.J.

[21] Appl. No.: 95,130

[22] Filed: Jul. 20, 1993

[51] Int. Cl.$^6$ .................. A61K 9/16; A61K 9/20
[52] U.S. Cl. ............ 424/451; 424/456; 424/463; 424/464; 424/499; 424/500; 424/501
[58] Field of Search ........................ 424/463, 464, 424/489, 499, 500, 501

[56] References Cited

U.S. PATENT DOCUMENTS

| | | | |
|---|---|---|---|
| 4,777,050 | 10/1988 | Vadino | 424/499 |
| 5,023,089 | 6/1991 | Sakamoto et al. | 424/489 |
| 5,110,605 | 5/1992 | Acharya | 424/499 |
| 5,126,145 | 6/1992 | Evenstad et al. | 424/499 |

*Primary Examiner*—Amy Hulina
*Attorney, Agent, or Firm*—Ralph R. Palo

[57] ABSTRACT

A granulation process for preparing a solid dosage form containing acetaminophen and diphenhydramine hydrochloride, as active agents is disclosed. In addition, the solid dosage form produced by the process is described.

11 Claims, No Drawings

GRANULATION PROCESS FOR PRODUCING AN ACETAMINOPHEN AND DIPHENHYDRAMINE HYDROCHLORIDE COMPOSITION AND COMPOSITION PRODUCED BY SAME

BACKGROUND OF THE INVENTION

Products containing the analgesic acetaminophen and the sleep aid diphenhydramine hydrochloride have been marketed for a number of years. Such products are marketed in various final solid dosage forms including tablets, caplets and gelcaps. The process used to produce solid dosage forms which are then formed into a final solid dosage form generally comprises a single granulation process wherein acetaminophen and diphenhydramine hydrochloride together with certain excipients are dry blended and then granulated by spraying the dry blended material with a suitable binder such as starch while the dry blend is mixed in a granulator such as a Fielder granulator. The granulation so formed is then dried, milled and formed into one of a number of solid dosage forms by conventional processing. As used herein the term "solid dosage form" means the solid core component of a dosage form, which may then be processed into a final solid dosage form. In the case of a caplet, it is the core caplet without any coating. In the case of a gelcap, it is the core caplet without any precoat or gelatin coating. In the case of a tablet, it is the core tablet without any coating. Generally, the solid dosage form is the core component formed from a conventional compressing step of the granulation before it undergoes any further processing. The term "final solid dosage" form means a solid dosage form, which has undergone further processing, such as precoating, coating, gelatin coating, printing or the like.

The acetaminophen/diphenhydramine hydrochloride solid dosage forms produced by this process possess inadequate hardness, generally about 7 kp or less. As a result, the solid dosage forms may become damaged during processing and packaging. This creates quality control problems and increases production costs. Another problem with this process is that the solid dosage forms produced possess a relatively high friability of greater than 1.0%.

Accordingly, it is an object of the present invention to develop a process which produces a medicament which when made into a solid dosage form has an adequate hardness of greater than 7 kp and preferably of from about 9–12 kp and a friability of less than about 1%.

SUMMARY OF THE INVENTION

The present invention is directed to a process for preparing a medicament comprising acetaminophen and diphenhydramine hydrochloride for use in forming a solid dosage form, wherein the process comprises:

(1) blending together acetaminophen, a filler, a disintegrant and an other excipient to form a dry blend;

(2) spraying a first binder into a granulator containing the dry blend formed in step (1) while the dry blend is being mixed so as to form a wet granulation;

(3) partially drying the wet granulation formed in step (2);

(4) spraying a solution/suspension of diphenhydramine hydrochloride ("DPH") into the granulator containing the partially dried granulation formed in step (3) while the granulation is being mixed;

(5) spraying a second binder selected from the group consisting of hydroxypropyl methylcellulose ("HPMC"), polyvinyl pyrrolidone ("PVP") and pregelantinized starch into the granulator containing the granulation of step (4); and (6) drying the granulation of step (5) so as to form a granulated medicament.

The granulation medicament so formed may then be subjected to further conventional processing to form various solid dosage forms including a tablet, caplet and gelcap. The resulting solid dosage forms have a hardness of from about 9–12 kp and more preferably 10–12 kp and a friability of less than about 1.0%. As used herein, the term caplet refers to solid oblong tablets which are sometimes coated with a material such as polymeric coating such as HPMC. A gelcap is a caplet which contains an outer gelatinous coating. The solid dosage forms may then be processed into final dosage forms by conventional techniques.

The present invention is also directed to the solid dosage forms produced by the process described herein.

DETAILED DESCRIPTION OF THE INVENTION

In the first step of the process of the present invention acetaminophen, a filler, a disintegrant and an other excipient are dry blended by conventional techniques. Optionally, but preferably a binder/disintegrant may be added to the dry blend. Suitable fillers include powdered cellulose, microcrystalline cellulose, starch, lactose and mannitol. Preferably, powdered cellulose is used. Sodium starch glycolate, sodium carboxymethylcellulose, sodium lauryl sulfate, and pregelantinized starch are examples of the disintegrant that may be used, with sodium starch glycolate being presently preferred. A suitable other excipient is sodium citrate anhydrous powder. Pregelantinized starch may be used as the optional binder/disintegrant.

The relative proportions of ingredients will depend upon the specific components being used. However, in all cases, for any given dosage strength of acetaminophen; e.g., 325 mg, 500 mg, etc.; it is desirable to use the least amount of excipients as is possible to form a suitable solid dosage form so as to produce the smallest possible solid dosage form. Generally, the acetaminophen is present in an amount of from about 75 to 85% by weight of the solid dosage form. The filler is present in an amount of from about 3 to 20% by weight, the other excipient is present in an amount of from about 0.1 to 1.0% by weight and the disintegrant is present in an amount of from about 1 to 4% by weight. The optional binder/disintegrant is present in an amount of from about 0 to 5% by weight.

The binder which is sprayed in step (2) of the process is first prepared as a solution or suspension by mixing a suitable binder in water so as to form a solution or suspension (hereinafter "solution/suspension") containing of from about 5 to 10% by weight solids. Suitable binders include starch, HPMC, PVP and pregelantinized starch. The binder is generally present in an amount of from about 4 to 10 % by weight of the solid dosage form. Preferably, starch is used. In the case of starch, it is mixed with water using a high speed mixer to form a solution/suspension containing about 7% by weight solids. The solution/suspension is heated to a temperature of from about 70° to 86° C., but preferably about 82° to 84° C. Heating may not be required when using pregelatinized starch or other binders. The binder solution/suspension is ready for spraying into the dry blend prepared in step (1). The dry blend components used in step (1) are first placed in a granulator such as fluid bed granulator or a high shear granulator. It is presently preferred to use a fluid bed granulator such as one made by Aeromatic or Glatt and high shear granulator such as a Fielder. While being mixed the binder solution/suspension is sprayed into the granulator to form a wet granulation. Depending upon the granulator being used and the batch size the granulation step (2) may take from about ¼ to 6 hours for batch sizes ranging from about 15 kg to 1000 kg, respectively. A fluid bed granulator will generally require a longer period of granulation of from about 1 to 6 hours for batch sizes ranging from about 15 kg to 1000 kg, respectively. During granulation, it is desirable to maintain the moisture content at about 6 to 16% moisture. This may be accomplished by varying parameters such as temperature and spray rate.

After completing the granulation in step (2), the resulting wet granulation is dried by heating the air within the granulator so as to reduce the moisture content to about 1 to 5%, preferably 1-3%, moisture so as to produce a partially dried granulation.

The diphenhydramine hydrochloride which is sprayed in step (4) of the process is prepared as a water solution; preferably, a 23% solution of diphenhydramine hydrochloride. The diphenhydramine hydrochloride is generally present in an amount of from about 1 to 8% by weight of the solid dosage form. The diphenhydramine hydrochloride solution is sprayed into the granulator while the dried granulation of step (3) is being mixed. Preferably, the diphenhydramine hydrochloride solution is sprayed at a rate of about 3 kg/min for a 1000 kg batch, with an inlet air temperature during spraying being about 50°–65° C. This spraying step generally takes place over a period of from about ½ hr to 2 hrs. until all of the diphenhydramine hydrochloride is used thereby producing a granulation.

In step (5) of the process, a second binder, HPMC, PVP or pregelantinized starch is sprayed as a solution/suspension. This binder is generally present in an amount of from about 0.2 to 4% by weight of the solid dosage form. Preferably, HPMC is used as the binder in a water solution/suspension containing about 3.4% solids. Immediately after the completion of step (4) of the process and without drying of the granulation formed in step (4), the second binder is sprayed into the granulator containing the granulation of step (4) while the granulation is being mixed. Preferably, 5 HPMC is sprayed at a rate of about 3 kg/min. for a 1000 kg batch size until the HPMC solution/suspension is completely used. The inlet air temperature is of from about 50°–65° C., and preferably about 57° C.

Thereafter, the granulation formed in step (5) is dried to a moisture content of about 0.8 to 1.1%, moisture thereby forming a granulated medicament ready for further processing into a solid dosage form by conventional techniques known in the art. The three solid dosage forms presently preferred are a tablet, a caplet and a gelcap.

To form such a solid dosage forms the dried granulation is milled in a suitable milling device such as a Glatt Quick Sieve and a lubricant is metered into the device during milling. A suitable lubricant such as magnesium stearate, calcium stearate or stearic acid, is used in an amount of from about 0.2 to 1% by weight of the solid dosage form. In addition, a dye and microcrystalline cellulose may be metered in at this point of the process. The resulting milled granulation is then blended and compressed into the solid dosage form by conventional techniques known in the art.

When a caplet is the desired final solid dosage form, the same general procedure is used as described above. Thereafter, the milled granulation is compressed into a caplet by conventional processing techniques. The caplet may then be coated with a coat of a suitable coating material such as HPMC which may contain a dye. Optionally, a wax coating may be added using, for example, Carnauba Wax. To produce a gelcap, the same procedures described previously to produce a caplet are employed except that the coating that is applied is applied as a precoat and then the gelatin coating is applied by conventional techniques known in the art. Other conventional processing may be used to produce these or other final dosage forms.

The solid dosage form produced by the process of the present invention generally comprises of from about 75 to 85% acetaminophen, more preferably about 79%, of from about 1 to 8% diphenhydramine hydrochloride, more preferably about 4.0%, of from about 1 to 4% of the disintegrant, more preferably about 1.6%, of from about 3 to 20% of the filler, more preferably about 6.3%, of from about 4.2 to 14% binder, more preferably about 6.6% of from about 0.1 to 1.0% of the other excipient, more preferably about 0.5%, and of from about 0.2 to 1% of a lubricant, more preferably about 0.5%, with all % being by weight of the solid dosage form. The binder represents the total binder present whether added in step (2) or step (5). The presently preferred solid dosage form will contain a binder comprising starch and at least one other binder selected from any of HPMC, PVP and pregelatinized starch.

The following Examples further illustrate the present invention. Each Example represents the production of at least 12,000 solid dosage forms of the same formulation.

EXAMPLE 1—TABLET

This Example 1 describes the preparation of a tablet solid dosage form using the process of the present invention. Table 1 shows the ingredients present in a 500 mg acetaminophen dosage tablet. The components used in the process of the invention are shown in the sections headed Dry Blend, Binder Spray Solution/Suspension, First Spray Solution and Second Spray Solution/Suspension. The Milled Dry Blend components are part of the conventional processing used to form the tablet.

TABLE 1

| INGREDIENT | AMOUNT (mg/dose) |
| --- | --- |
| Dry Blend | |
| Acetaminophen USP | 500.00 |
| Powdered Cellulose NF | 40.00 |
| Sodium Starch Glycolate NF | 10.00 |
| Sodium Citrate Anhydrous Powder, USP | 3.00 |
| Starch Pregelatinized NF | 10.00 |
| Binder Spray Solution/Suspension | |
| Purified Water USP to form a (7% solution) of starch | — |
| Starch NF (Cornstarch) | 40.00 |
| First Spray Solution | |
| Diphenhydramine Hydrochloride, Crystalline, USP | 25.0 |
| Purified Water USP (to prepare 23% solution of DPH) | — |
| Second Spray Solution/Suspension | |
| Hydroxypropyl Methylcellulose 2910 USP - 15 centipoise | 1.5 |
| Purified Water USP (to prepare 3.4% solution of HPMC) | — |
| Milled Dry Blend | |
| (FD&C #1 HT Al Lake (13%) Certified | 0.84 |

TABLE 1-continued

| INGREDIENT | AMOUNT (mg/dose) |
|---|---|
| Microcrystalline Cellulose NF | 2.00 |
| Magnesium Stearate NF | 3.2 |
| Total Weight | 635.54 mg |

The tablet was produced by first forming a dry blend of each of the components listed in Table 1 under the heading Dry Blend. The dry blend components were then placed in a Glatt fluid bed granulator. The Binder Spray Solution/Suspension was then separately prepared by adding the starch to water at room temperature. The solution/suspension was mixed with a high speed mixer for 5 minutes after all the starch had been added. The solution/suspension was then heated to a temperature of between about 82°–84° C. with gentle mixing.

The dry blend components in the Glatt fluid bed granulator was then fluidized and the Binder Spray Solution/Suspension was then sprayed into the fluid bed granulator effecting granulation The processing conditions of the starch spraying are shown in Table 2.

The resulting wet granulation was then dried by heating the wet granulation to a temperature of about 37°–45° C. to reduce the moisture content to between about 1.0 –2.5%. Thereafter, the First Spray Solution was sprayed into the granulator while the granulation formed previously was fluidized. This spraying was carded out until all of the DPH solution was used. Immediately thereafter the Second Spray Solution/Suspension was sprayed into the granulator until the granulation therein was fluidized and the solution/suspension was used up. The resulting granulation was then dried by heating up to about 50° C. exhaust temperature to reduce the moisture content to about 0.8–1.1%. The spray conditions for both the DPH solution and HPMC solution/suspension spraying are shown in Table 3.

TABLE 2

STARCH SPRAY CONDITIONS

| | |
|---|---|
| Product Bowl Supporting Screen Open Area | 4.0% |
| Nozzle Port Opening | 3.0 mm |
| Nozzle Assembly Position in Expansion Chamber | Middle Position, Side Entry |
| Inlet Air Temp. Set Point - During Granulation | 80° C. (Range: 73° C.–87° C.) |
| Product Temp before beginning to spray starch paste | 42° C.–44° C. |
| Starch spray rate | 6.5 kg/min. (Range: 6.3–6.7) |
| Atomization Air Pressure (outlet) | 5.0 BAR (range: 4.8–5.2 BAR) |
| Inlet Air Flap Setting | 100% |
| Spray Time Setting (Actual Pumping Time) | 3 min (Range: 2–3 min.) |
| Shake Time Setting | 15 sec; (Range: 10–20 sec.) |
| Debro Reading For Air Flow, (Debro Reading X1000) | |
| Pre blend Cycle | 12–13 m³/hr. |
| Drying Cycle | 15–16 m³/hr. |
| Inlet Air Temp. Set Point - "Drying Cycle" | 87° C. |
| Granulation Moisture Content After Drying | 1.0–2.5% |

TABLE 3

DPH AND HPMC SPRAY CONDITIONS

| | |
|---|---|
| Product Bowl Supporting Screen Open Area | 4.0% |
| Nozzle Port Opening | 3.0 mm |
| Nozzle Assembly Position in Expansion Chamber | Middle Position, Side Entry |
| Inlet Air Temp. Set Point - During Granulation | 57° C. (Range: 50° C.–65° C. |
| Product Temp before beginning to spray starch paste | 37° C.–45° C. |
| DPH Starch Spray Rate | 3.0 kg/min. (Range: 2.8–3.2) |
| HPMC Spray Rate | 3.0 kg/min. (Range: 2.8–3.2) |
| Atomization Air Pressure (outlet) | 6 BAR (range: 5.8–6.2 BAR) |
| Inlet Air Flap Setting | 100% |
| Spray Time Setting (Actual Pumping Time) | 3 min (Range: 2–3 min.) |
| Shake Time Setting | 15 sec; (Range: 10–20 sec.) |
| Debro Reading For Air Flow, (Debro Reading X1000) | |
| Spray Cycle | 12–13 m³/hr. |
| Drying Cycle | 12–13 m³/hr. |
| Inlet Air Temp. Set Point - "Drying Cycle" | 57° C. |
| Granulation Moisture Content After Drying | 0.8–1.1% |

The remainder of the process for producing the tablet involves conventional processing techniques. Generally, the dried granulation was milled in a Glatt Quick Sieve while the lubricant magnesium stearate NF and a dye mixture of FD&C #1 HT AI Lake (13%) certified and microcrystalline cellulose NF was metered in the mill. The resulting granulation was then pressed into a tablet using a Beta tablet press, with precompression. The resulting tablet had the properties shown in Table 4.

TABLE 4

Description: Light blue, round; 15/32" FFBE.
Original Physical Observations:

| Test | Observation |
|---|---|
| Average core weight: | 633.8 mg |
| Thickness: | 5.13 mm |
| Hardness: | 14.2 kp |
| Friability, 100 drops, 4 min: | <0.1% |

In this example and each of these examples in this application hardness was measured using a hardness tester manufactured by Schleuniger Productronic A. G, Model 4-M. The hardness was measured by placing ten solid dosage forms in the tester, one at a time, and measuring the hardness. The reported value represents the average value. In the case of elongated tablets such as caplets the elongated tablets were perpendicularly positioned in the hardness tester so that the stress is placed on the ends of the tablet.

Friability was tested using a Vanderkamp friabilator manufactured by Van-Kel Industries Inc. For the tablet, 20 solid dosage forms were rotated in the friabilator for 4 minutes at 25 RPM. For the caplet and gelcap, 20 solid dosage forms were rotated in the friabilator for 16 minutes at 25 RPM.

EXAMPLE 2—GELCAP

This Example 2 describes the preparation of a gelcap using the process of the present invention. Table 5 shows the components used to form the gelcap. The Milled Dry Blend granulation, Precoat and Gelatin Coating relate to conventional processing to form the gelcap from the granulation prepared according to the process of the present invention.

TABLE 5

| INGREDIENT | AMOUNT (mg/dose) |
|---|---|
| Dry Blend | |
| Acetaminophen USP | 500.00 |
| Powdered Cellulose NF | 40.00 |
| Sodium Starch Glycolate NF | 10.00 |
| Sodium Citrate Anhydrous Powder, USP | 3.00 |
| Starch Pregelatinized NF | 10.00 |
| Binder Spray Solution/Suspension | |
| Purified Water USP to form a (7% solution) of starch | — |
| Starch NF (Cornstarch) | 40.00 |
| First Spray Solution | |
| Diphenhydramine Hydrochloride, Crystalline, USP | 25.0 |
| Purified Water USP (to prepare 23% solution of DPH) | — |
| Second Spray Solution/Suspension | |
| Hydroxypropyl Methylcellulose 2910 USP - 15 centipoise | 1.5 |

TABLE 5-continued

| INGREDIENT | AMOUNT (mg/dose) |
|---|---|
| Purified Water USP (to prepare 3.4% solution of HPMC) | — |
| Milled Dry Blend | |
| Magnesium Stearate NF | 3.2 |
| Total Uncoated Gelcap Core Weight (solid dosage form): mg | 632.7 |

The processing conditions and equipment used to produce the granulation for the gelcap are the same as described in Example 1, except that an Aeromatic fluid bed granulator was used in steps (4)–(6). The granulation so formed was thereafter milled in a Glatt Quick Sieve mill and the lubricant magnesium stearate NF was metered into the mill. The resulting granulation was then formed into a caplet using a Fette P-1000 tablet press. Finally, a precoat and a gelatin coating were applied. The caplet had the physical property shown in Table 6. It was later formed into a gelcap by conventional processing techniques.

TABLE 6

Description: Capsule-shaped, gelatin coated tablet. Core dimensions; 0.750" x 0;250", x 0.002" blended land. Bicolored; cap dark blue, body light blue.
Original Physical Observations:

| Test | Observation |
|---|---|
| Average core weight: | 633.0 mg |
| Thickness: | 6.25 mm |
| Hardness: | 9.4 kp |
| Friability, 400 drops, 16 min: | <0.1% |

EXAMPLE 3—CAPLET

This Example 3 describes the preparation of a caplet using the process of the present invention. Table 7 shows the components used to form the caplet. The Milled Dry Blend components relate to conventional processing to form the caplet from the granulation prepared according to the present invention.

TABLE 7

| INGREDIENT | AMOUNT (mg/dose) |
|---|---|
| Dry Blend | |
| Acetaminophen USP | 500.00 |
| Powdered Cellulose NF | 40.00 |
| Sodium Starch Glycolate NF | 10.00 |
| Sodium Citrate Anhydrous Powder, USP | 3.00 |
| Starch Pregelatinized NF | 10.00 |
| Binder Spray Solution/Suspension | |
| Purified Water USP to form a (7% solution) of starch | — |
| Starch NF (Cornstarch) | 40.00 |
| First Spray Solution | |
| Diphenhydramine Hydrochloride, Crystalline, USP | 25.0 |
| Purified Water USP (to prepare 23% solution of DPH) | — |
| Second Spray Solution/Suspension | |

TABLE 7-continued

| INGREDIENT | AMOUNT (mg/dose) |
|---|---|
| Hydroxypropyl Methylcellulose 2910 USP - 15 centipoise | 1.5 |
| Purified Water USP (to prepare 3.4% solution of HPMC) | — |
| Milled Dry Blend | |
| Magnesium Stearate NF | 3.2 |
| Total Uncoated Core Weight(solid dosage form) | 632.7 mg |

The processing conditions and equipment used to produce the granulation were the same as described in Example 1. The granulation so formed was thereafter milled in a Glatt Quick Sieve while magnesium stearate NF was metered into the mill. The resulting milled granulation was then formed into a caplet using a Fette P-3100 tablet press, with precompression. The physical properties of the caplet are shown in Table 8. The caplet was later film coated followed by application of a wax film.

TABLE 8

Description: Caplet-shaped. Core dimensions; 0.6875" × 0.2812" × 0.070".
Original Physical Observations:

| Test | Observation |
|---|---|
| Average core weight: | 633.4 mg |
| Thickness: | 6.10 mm |
| Hardness: | 11.5 kp |
| Friability, 400 drops, 16 min: | <0.1% |

We claim:

1. A process for preparing a medicament comprising acetaminophen and diphenhydramine hydrochloride for use in forming a suitable dosage form, wherein the process comprises:

(a) blending together acetaminophen, a filler and a disintegrant to form a dry blend;

(b) spraying a binder into a granulator containing the dry blend formed in step (a) while the dry blend is being mixed so as to form a wet granulation;

(c) partially drying the wet granulation of step (b);

(d) spraying a solution of diphenhydramine hydrochloride into the granulator containing the partially dried granulation of step (c) while the partially dried granulation is being mixed;

(e) spraying a binder selected from the group consisting of hydroxypropyl methylcellulose, polyvinyl pyrrolidone and pregelatinized starch into the granulator containing the granulation of step (d);

(f) drying the granulation of step (e) so as to form the granulated medicament.

2. The process of claim 1, further comprising adding a lubricant and milling the granulated medicament and thereafter forming the milled medicament into a dosage form selected from the group consisting of a caplet, a tablet and a gelcap.

3. The process of claim 1, wherein the dosage form is a caplet.

4. The process of claim 1, wherein the dosage form is a tablet.

5. The process of claim 1, wherein the dosage form is a gelcap.

6. The process of claim 1, wherein the filler is selected from any of powdered cellulose, microcrystalline cellulose, starch, lactose or mannitol.

7. The process of claim 1, wherein the disintegrant is selected from any of sodium starch glycolate, sodium carboxymethylcellulose, sodium lauryl sulfate or pregelatinized starch.

8. The process of claim 1, wherein the binder is selected from any of starch, hydroxypropyl methylcellulose, polyvinyl pyrrolidone or pregelatinized starch.

9. The process of claim 1, wherein in step (e) the binder is hydroxypropyl methylcellulose.

10. The process of claim 1, wherein the granulated medicament is dried to a moisture content of about 0.8 to 1.1%.

11. The process of claim 1, wherein in step (c) the wet granulation is partially dried to a moisture content of about 1.0 to 5.0%.

* * * * *